US 12,202,935 B2

(12) United States Patent
Hsu et al.

(10) Patent No.: US 12,202,935 B2
(45) Date of Patent: Jan. 21, 2025

(54) RESIN COMPOUND AND RESIN COMPOSITION CONTAINING THE SAME

(71) Applicant: INDUSTRIAL TECHNOLOGY RESEARCH INSTITUTE, Hsinchu (TW)

(72) Inventors: Meei-Yu Hsu, Hsinchu (TW); Chih-Hao Lin, Taoyuan (TW); Kai-Chi Chen, Nantou County (TW); Yi-Chun Chen, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 401 days.

(21) Appl. No.: 17/590,530

(22) Filed: Feb. 1, 2022

(65) Prior Publication Data

US 2023/0174709 A1 Jun. 8, 2023

(30) Foreign Application Priority Data

Dec. 3, 2021 (TW) ................................. 110145160

(51) Int. Cl.
C08G 61/12 (2006.01)
C07C 13/61 (2006.01)

(52) U.S. Cl.
CPC .............. C08G 61/12 (2013.01); C07C 13/61 (2013.01); C07C 2602/26 (2017.05); *C08G 2261/135* (2013.01); *C08G 2261/312* (2013.01); *C08G 2261/3325* (2013.01); *C08G 2261/344* (2013.01)

(58) Field of Classification Search
CPC ........................ C08G 61/12; C08G 2261/3325; C07C 13/61; C07C 2602/26
See application file for complete search history.

(56) References Cited

U.S. PATENT DOCUMENTS

| 2018/0170873 A1 | 6/2018 | Das et al. |
| 2019/0153151 A1 | 5/2019 | Cho et al. |
| 2019/0210967 A1 | 7/2019 | Das et al. |
| 2020/0325100 A1 | 10/2020 | Yamaguchi et al. |

FOREIGN PATENT DOCUMENTS

| CN | 102134431 B | | 8/2013 | |
| CN | 104629341 A | * | 5/2015 | ............. C08L 71/12 |
| CN | 107022075 A | | 8/2017 | |
| CN | 110655775 A | | 1/2020 | |
| CN | 112266572 A | | 1/2021 | |
| JP | 2018-24856 A | | 2/2018 | |
| JP | 2018024856 A | * | 2/2018 | ............. C08G 59/20 |
| TW | I471369 B | | 2/2015 | |
| TW | 201518403 A | * | 5/2015 | ............. C08G 61/02 |
| TW | I577732 B | | 4/2017 | |
| TW | I606076 B | | 11/2017 | |
| TW | 201741361 A | | 12/2017 | |
| TW | I621679 B | | 4/2018 | |
| TW | I638001 B | | 10/2018 | |
| TW | 201930458 A | | 8/2019 | |
| WO | WO-8905318 A1 | * | 6/1989 | ............... C08G 8/36 |
| WO | WO-9211580 A1 | * | 7/1992 | ........... C07C 43/215 |
| WO | WO-2021241255 A1 | * | 12/2021 | ............. B32B 27/12 |

OTHER PUBLICATIONS

Liao, Z.K.; Wang, C.S. "The synthesis and characterization of novel thermosettable vinylbenzyl terminated monomers and the properties of the cured resins." Polymer Bulletin 1989, 22, 1-7. (Year: 1989).*
TW 210518403A (May 16, 2015); machine translation. (Year: 2015).*

(Continued)

*Primary Examiner* — Rip A Lee

(74) *Attorney, Agent, or Firm* — Birch, Stewart, Kolasch & Birch, LLP

(57) ABSTRACT

A resin compound has a structure represented by a chemical formula (I):

(I)

In the chemical formula (I), each $R^1$ independently represents a $C_1$-$C_{20}$ alkylene group or a $C_7$-$C_{40}$ alkylarylene group, and $R^1$ are the same or different from each other; n independently represents an integer of 1-4; each $R^2$ independently represents a $C_1$-$C_{20}$ alkyl group or a $C_2$-$C_{20}$ terminal alkenyl group, and $R^2$ are the same or different from each other. When at least one of $R^1$ represents a $C_1$-$C_{20}$ alkylene group, at least one of $R^2$ is a $C_2$-$C_{20}$ terminal alkenyl group.

9 Claims, No Drawings

(56) References Cited

OTHER PUBLICATIONS

Taiwanese Office Action and Search Report for Taiwanese Application No. 110145160, dated Jun. 28, 2022.
Guo et al., "Fluorinated bismaleimide resin with good processability, high toughness, and outstanding dielectric properties", Journal of Applied Polymer Science, Jul. 30, 2015, app. 42791, total 8 pages.
Hwang et al., "Flame Retardancy and Dielectric Properties of Dicyclopentadiene-Based Benzoxazine Cured with a Phosphorus-Containing Phenolic Resin", Journal of Applied Polymer Science, Aug. 18, 2008, vol. 110, pp. 2413-2423.
Lin et al., "Low Dielectric Thermoset. I. Synthesis and Properties of Novel 2,6-Dimethyl phenol-dicyclopentadiene Epoxy", Journal of Applied Polymer Science, Jul. 29, 2002, vol. 88, pp. 2607-2613.
Shieh et al., "Synthesis and Properties of a Cyanate Ester Containing Dicyclopentadiene(II)", Journal of Polymer Science: Part A: Polymer Chemistry, Jul. 25, 2004, vol. 43, pp. 671-681.

\* cited by examiner

RESIN COMPOUND AND RESIN COMPOSITION CONTAINING THE SAME

CROSS REFERENCE TO RELATED APPLICATION

The present application is based on, and claims priority from, Taiwan Application Serial Number 110145160, filed Dec. 3, 2021, the disclosure of which is hereby incorporated by reference herein in its entirety.

TECHNICAL FIELD

The technical field relates to a resin compound and a resin composition containing the same.

BACKGROUND

5th generation mobile networks technology, 5G mobile networks for short, is the latest generation of mobile communication technology. 5G mobile communication technology has the characteristics of high-speed transmission, wide connection, and low latency. Recently, 5G mobile communication technology can be divided into three types: high-frequency 5G, intermediate-frequency 5G, and low-frequency 5G according to the frequency band used.

High-frequency 5G can provide ultra-high connection rates. However, the signal emission and reception quality of high-frequency 5G will be affected by high-frequency path loss, conductor loss, and dielectric loss during the signal transmission process. The dielectric loss is directly related to the packaging material. Therefore, it is necessary to develop packaging materials with low dielectric loss to reduce the dielectric loss of high-frequency 5G in the transmission process, thereby improving the signal emission and reception quality.

The proposal of reducing dielectric loss can be achieved by reducing the dielectric properties (dielectric constant (Dk)εr) and the dissipation factor (Df) of the packaging materials. Hydrocarbon resins or polyolefin materials composed of carbon atoms and hydrogen atoms have low dielectric loss characteristics due to the small number of polar functional groups.

SUMMARY

The present disclosure provides a resin compound having low dielectric loss characteristics, high mechanical properties, and high thermal stability, and a resin composition containing the same.

Some embodiments of the present disclosure provide a resin compound having a structure represented by a chemical formula (I):

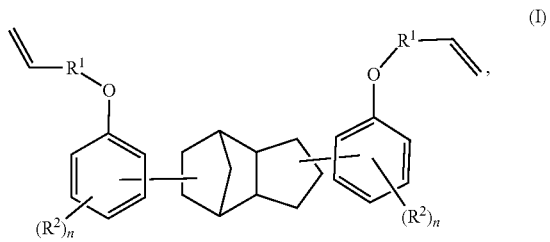

(I)

wherein each $R^1$ may independently represent a $C_1$-$C_{20}$ alkylene group or a $C_7$-$C_{40}$ alkylarylene group, and $R^1$ may be the same or different from each other; n may independently represent an integer of 1-4; each $R^2$ may independently represent a $C_1$-$C_{20}$ alkyl group or a $C_2$-$C_{20}$ terminal alkenyl group, and $R^2$ may be the same or different from each other. When at least one of $R^1$ represents a $C_1$-$C_{20}$ alkylene group, at least one of $R^2$ is a $C_2$-$C_{20}$ terminal alkenyl group.

Some embodiments of the present disclosure provide a resin composition containing the resin compound mentioned above.

DETAILED DESCRIPTION

The following description is made for the purpose of illustrating the general principles of the disclosed embodiments and should not be taken in a limiting sense. The scope of the disclosed embodiments is best determined by reference to the appended claims.

Unless otherwise defined, all terms (including technical and scientific terms) used herein have the same meaning as commonly understood by one of ordinary skill in the art to which the present disclosure belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

As used herein, the term "and/or" includes any and all combinations of one or more of the associated listed items. The use of "may" when describing embodiments of the present disclosure refers to "one or more embodiments of the present disclosure."

A $C_1$-$C_{20}$ alkyl group used herein refers to a linear or branched aliphatic hydrocarbon monovalent group having 1 to 20 carbon atoms in the main carbon chain, and examples thereof include but not limited to a methyl group, an ethyl group, a propyl group, an iso-butyl group, a sec-butyl group, a tert-butyl group, a pentyl group, an iso-amyl group, and a hexyl group. A $C_1$-$C_{20}$ alkylene group used herein refers to a divalent group having the same structure as the $C_1$-$C_{20}$ alkyl group. Examples of the $C_1$-$C_{20}$ alkylene group include but not limited to a methylene group, an ethylene group, a propylene group, an iso-butylene group, a sec-butylene group, a tert-butylene group, a pentylene group, an iso-amylene group, and a hexylene group.

A $C_2$-$C_{20}$ terminal alkenyl group used herein refers to a hydrocarbon group having at least one carbon-carbon double bond at a terminal end of a carbon chain of the $C_2$-$C_{20}$ alkyl group, and examples thereof include but not limited to an ethenyl group, a 2-propenyl group (n-propenyl group), and a 1-butenyl group.

A $C_7$-$C_{40}$ alkylarylene group used herein refers to a divalent group including a structure represented by —$R^a$Ar—, wherein $R^a$ represents $C_1$-$C_{20}$ alkylene group as mentioned above, Ar represents $C_6$-$C_{20}$ arylene group. $C_6$-$C_{20}$ arylene group used herein refers to a divalent group including a carbocyclic aromatic system having 6 to 20 carbon atoms. Examples of the $C_6$-$C_{20}$ aryl group include but not limited to a phenylene group, a naphthylene group, an anthracenylene group, and a phenanthrenylene group. Examples of the $C_7$-$C_{40}$ alkylarylene group include but not limited to a methylphenylene group, an ethylphenylene group, a propylphenylene group, a pentylphenylene group, a hexylphenylene group, and a methylnaphthylene group.

The present disclosure provides a resin compound having a structure represented by a chemical formula (I):

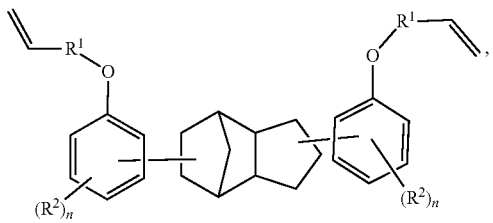

(I)

wherein each $R^1$ may independently represent a $C_1$-$C_{20}$ alkylene group or a $C_7$-$C_{40}$ alkylarylene group, and $R^1$ may be the same or different from each other; n may independently represent an integer of 1-4; each $R^2$ may independently represent a $C_1$-$C_{20}$ alkyl group or a $C_2$-$C_{20}$ terminal alkenyl group, and $R^2$ may be the same or different from each other. When at least one of $R^1$ represents a $C_1$-$C_{20}$ alkylene group, at least one of $R^2$ is a $C_2$-$C_{20}$ terminal alkenyl group. In an embodiment, each $R^1$ may independently represent a $C_1$-$C_6$ alkylene group or a $C_7$-$C_{10}$ alkylarylene group, and each $R^2$ may independently represent a $C_1$-$C_6$ alkyl group or a $C_2$-$C_6$ terminal alkenyl group. In an embodiment, each $R^1$ may independently represent a methylene group, an ethylene group, a propylene group, an iso-butylene group, a sec-butylene group, a tert-butylene group, a pentylene group, an iso-amylene group, a hexylene group, a methylphenylene group, a ethylphenylene group, a propylphenylene group, a pentylphenylene group, a hexylphenylene group, or a methylnaphthylene group. In an embodiment, each $R^2$ may independently represent a methyl group, an ethyl group, a propyl group, an iso-butyl group, a sec-butyl group, a tert-butyl group, a pentyl group, an iso-amyl group, a hexyl group, an ethenyl group, a 2-propenyl group, or a 1-butenyl group.

The resin compound of the present disclosure has a dicyclopentadiene core structure, a benzene ring, a polymerizable functional group, and an ether oxygen. The dicyclopentadiene core structure has low dielectric properties. The benzene ring may improve the heat resistance, reduce the dielectric constant, and reduce the dielectric loss of the resin compound of the present disclosure.

The resin compound of the present disclosure is a viscous liquid at room temperature. The ether oxygen may improve the adhesive force of the resin compound of the present disclosure. By the inclusion of the ether oxygen, the viscosity of the resin compound of the present disclosure may be 100-200 Pa·s at 25° C. In an embodiment, the viscosity of the resin compound of the present disclosure may be 110-150 Pa·s at 25° C. The viscosity of the resin compound of the present disclosure may be 1-20 Pa·s at 50° C. In an embodiment, the viscosity of the resin compound of the present disclosure may be 5-10 Pa·s at 50° C. Based on the viscosity characteristics mentioned above, the resin compound of the present disclosure has high adhesive force. Based on the liquid characteristics and the high adhesion characteristics mentioned above, the resin compound of the present disclosure may be suitable for application as a solvent-free liquid semiconductor packaging material.

In an embodiment, a resin compound of the present disclosure may have a structure represented by a chemical formula (II):

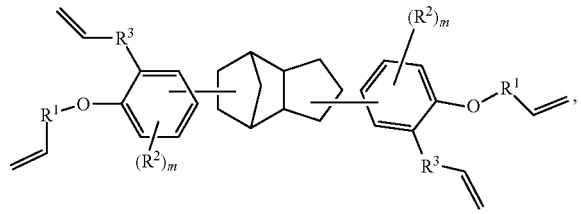

(II)

wherein each $R^1$ may independently represent a $C_1$-$C_{20}$ alkylene group or a $C_7$-$C_{40}$ alkylarylene group, and $R^1$ may be the same or different from each other. Each $R^2$ may independently represent a $C_1$-$C_{20}$ alkyl group or a $C_2$-$C_{20}$ terminal alkenyl group, m may independently represent an integer of 0-3 and $R^2$ may be the same or different from each other. Each $R^3$ may independently represent a single bond or a $C_1$-$C_{18}$ alkylene group, and $R^3$ may be the same or different from each other. In an embodiment, each $R^2$ may independently represent a $C_1$-$C_6$ alkyl group or a $C_2$-$C_6$ terminal alkenyl group. In an embodiment, each $R^2$ may independently represent a methyl group, an ethyl group, a propyl group, an iso-butyl group, a sec-butyl group, a tert-butyl group, a pentyl group, an iso-amyl group, a hexyl group, an ethenyl group, a 2-propenyl group, or a 1-butenyl group.

The resin compound represented by the chemical formula (II) has at least four arms that may undergo radical polymerization, and therefore has high crosslinking reactivity. The resin compound represented by the chemical formula (II) may react with the crosslinking agent to form a network structure after curing. Accordingly, after curing, the dissipation factor (Df) and dielectric properties (Dk) of a resin composition containing the resin compound may be further reduced and the dielectric stability and the thermal stability of the resin composition may be improved. Therefore, the purpose for reducing the dielectric constant, reducing the dielectric loss, and improving the reliability of the resin composition may be achieved.

In an embodiment, a resin compound of the present disclosure may have a structure represented by a chemical formula (II-1):

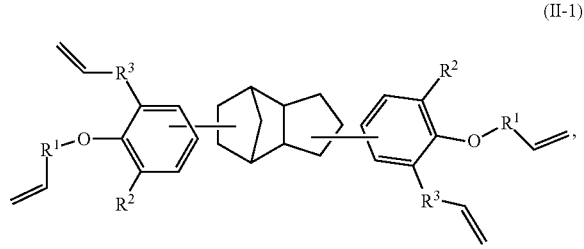

(II-1)

wherein each $R^1$ may independently represent a $C_1$-$C_{20}$ alkylene group or a $C_7$-$C_{40}$ alkylarylene group; each $R^2$ may independently represent a $C_1$-$C_{20}$ alkyl group or a $C_2$-$C_{20}$ terminal alkenyl group; each $R^3$ may independently represent a single bond or a $C_1$-$C_{18}$ alkylene group. $R^1$ may be the same or different from each other. $R^2$ may be the same or different from each other. $R^3$ may be the same or different from each other.

In an embodiment, a resin compound of the present disclosure may have a structure represented by a chemical formula (II-2):

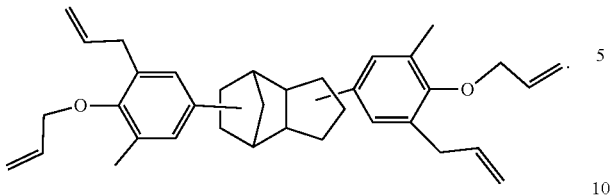

(II-2)

In other embodiments, a resin compound of the present disclosure may have a structure represented by a chemical formula (III):

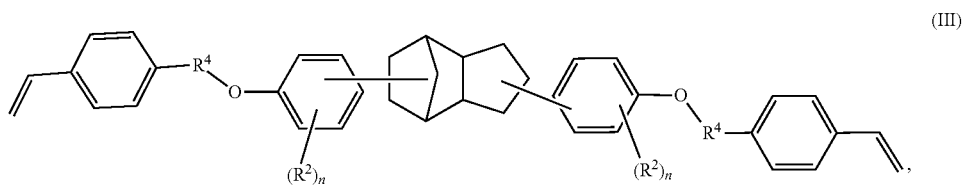

(III)

wherein each $R^2$ may independently represent a $C_1$-$C_{20}$ alkyl group or a $C_2$-$C_{20}$ terminal alkenyl group; each $R^4$ may independently represent a $C_1$-$C_{34}$ alkylene group; n may independently represent an integer of 1-4; and $R^2$ may be the same or different from each other and $R^4$ may be the same or different from each other. In an embodiment, each $R^2$ may independently represent a $C_1$-$C_6$ alkyl group or a $C_2$-$C_6$ terminal alkenyl group. In an embodiment, each $R^2$ may independently represent a methyl group, an ethyl group, a propyl group, an iso-butyl group, a sec-butyl group, a tert-butyl group, a pentyl group, an iso-amyl group, a hexyl group, an ethenyl group, a 2-propenyl group, or a 1-butenyl group.

The resin compound represented by the chemical formula (III) has at least two arms that may undergo radical polymerization, and the least two arms have 4-vinylphenyl structures with high reactivity. Therefore, the resin compound has high crosslinking reactivity. The resin compound represented by the chemical formula (III) may react with the crosslinking agent to form a network structure after curing. Accordingly, after curing, the dissipation factor (Df) and dielectric properties (Dk) of a resin composition containing the resin compound may be further reduced and the dielectric stability and the thermal stability of the resin composition may be improved. Therefore, the purpose for reducing the dielectric constant, reducing the dielectric loss, and improving the reliability of the resin composition may be achieved.

In an embodiment, a resin compound of the present disclosure may have a structure represented by a chemical formula (III-1):

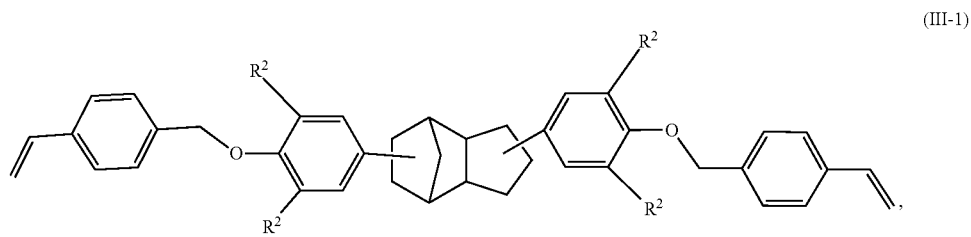

(III-1)

wherein each $R^2$ may independently represent a $C_1$-$C_{20}$ alkyl group and $R^2$ may be the same or different from each other.

In an embodiment, a resin compound of the present disclosure may have a structure represented by a chemical formula (III-2):

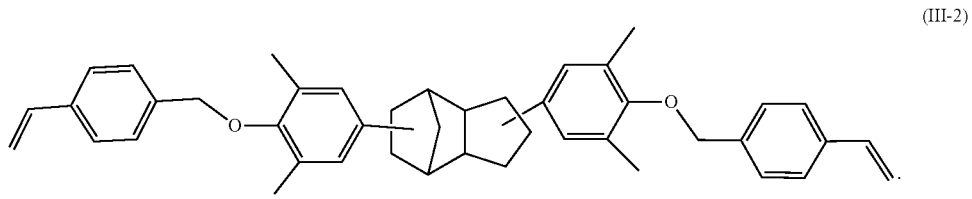

(III-2)

The present disclosure provides a resin composition containing the resin compound mentioned above.

According to an embodiment, the resin composition further comprises a crosslinking agent. The crosslinking agent may be selected from a group consisting of a divinylbenzene (DVB), a 4-tert-butoxystyrene (tBOS), a triallyl isocyanurate (TAIC), a triallyl cyanurate (TAC), and a 2,2-bis[3-allyl-4-(4-vinylbenzyl)phenyl]propane (AV-BPA). AV-BPA is represented by the following formula:

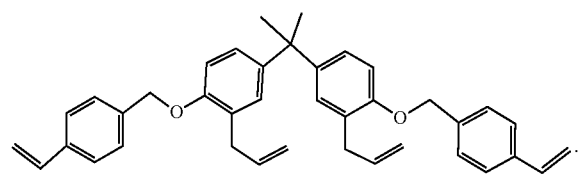 [SMILES: C=CCc1cc(C(C)(C)c2ccc(OCc3ccc(C=C)cc3)c(CC=C)c2)ccc1OCc1ccc(C=C)cc1]

The resin composition of the present disclosure has low dissipation factor (Df) and dielectric constant (Dk), good dielectric stability and good heat resistance between 10-80 GHz, and may meet the requirement of low dielectric loss at high frequencies. Therefore, the resin composition of the present disclosure is suitable for application as a high-frequency packaging material.

The resin composition of the present disclosure is in a liquid state at room temperature. The viscosity of the resin composition of the present disclosure may be 1000-5000 cps at 25° C. In an embodiment, the viscosity may be 1000-3000 cps at 25° C. Based on the viscosity characteristics mentioned above, the resin composition of the present disclosure may be suitable for application as a solvent-free liquid semiconductor packaging material.

One or more embodiments of the present disclosure will now be described in detail with reference to the following examples. However, these examples are only used to illustrate the embodiments of the present disclosure and are not intended to limit the scope of the embodiments of the present disclosure.

Synthesis Example 1

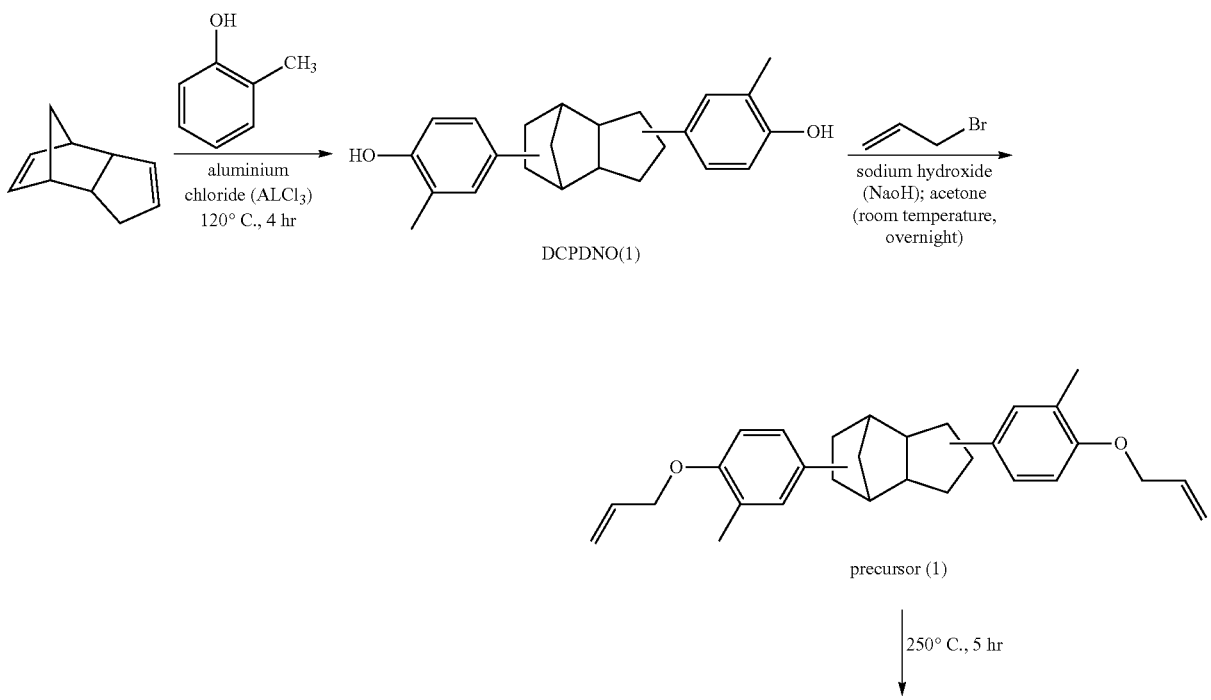

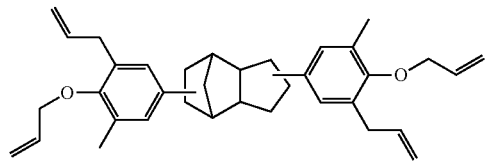

resin compound (1)

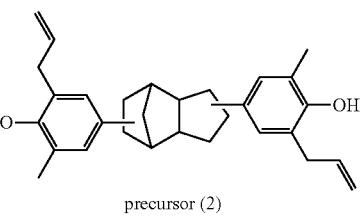

precursor (2)

Step 1

77.1 g (0.7143 mol) of o-cresol (2-(CH$_3$)C$_6$H$_4$OH) and 2 g (0.015 mol) of aluminum chloride (AlCl$_3$) were added into a 250 ml round-bottomed reaction flask. The reaction flask was heated to 100° C. and the above-mentioned compounds were uniformly mixed to obtain a mixture after introducing nitrogen gas and placing a stir bar into the flask. After gradually heating the mixture to 120° C., 13.2 g (0.1 mol) of dicyclopentadiene (DCPD) was slowly added into the mixture within 2 hours, and then a reaction was conducted at 120° C. for 4 hours. After the reaction was completed, 5 mol % sodium hydroxide aqueous solution containing 2.4 g of sodium hydroxide (NaOH) was added into the mixture and the mixture was stirred for 1 hour further to obtain a reaction mixture. The resulting reaction mixture was filtered, and the filtrate was washed with water 3 times. The organic phase was distilled to remove excess 2,6-dimethylphenol, dissolved in toluene, extracted 3 times with water, and drained to obtain 32 g of dark brown solid, a dicyclopentadiene phenol novolac (1) (DCPDNO (1)).

Step 2

32 g of DCPDNO(1) and 400 g of acetone were added into a 1000 ml round bottom reaction flask. 5.49 g of NaOH was added and the mixture was stirred after introducing nitrogen gas and placing a stir bar into the flask. After 30 min of stirring, 16.64 g of allyl bromide was added into the flask, then a reaction was conducted at room temperature overnight. After the reaction was completed, the reaction solution was filtered to remove the solids, and the filtrate was drained to obtain a dried crude product. The dried crude product was dissolved in dichloromethane, and extracted 3 times with water. The organic phase was drained again to give 33 g of dark brown liquid, a 4-arm precursor (1).

Step 3

33 g of the 4-arm precursor (1) was placed into a 150 ml round-bottom reaction flask and heated to a temperature between 240-250 degrees C. under nitrogen. The temperature was maintained for 5 hours to conduct a transposition reaction of allyl group. A 4-arm precursor (2) was obtained after completing the reaction.

Step 4

33 g of 4-arm precursor (2) and 350 g of acetone were added into a 1000 ml round-bottom reaction flask. 5.67 g of NaOH was added and the mixture was stirred after introducing nitrogen gas and placing a stir bar into the flask. After 30 min of stirring, 17.22 g of allyl bromide was added into the flask, then a reaction was conducted at room temperature overnight. After the reaction was completed, the reaction solution was filtered to remove the solids, and the filtrate was drained to obtain a dried crude product. The dried crude product was dissolved in dichloromethane and extracted 3 times with water. The organic phase was drained again to obtain a dark brown liquid, 4-arm resin compound (1).

The physical measurement of the compound 4-arm resin compound (1) is listed below: 1H NMR (500 MHz, CDCl$_3$): 1.10~2.48 (m, 20H), 3.34 (br.s, 4H), 4.32 (br.s, 4H), 4.95~5.15 (m, 4H), 5.25 (br.s, 2H), 5.45 (br.t, 2H), 5.85~6.05 (m, 2H), 6.05~6.20 (m, 2H), 6.05~7.20 (m, 4H).

The viscosity of the 4-armed resin compound (1) at 25° C. was measured with a rheometer (BROOKFIELD-87333). The viscosity of the 4-armed resin compound (1) was 116 Pa·s at 25° C. The viscosity of the 4-armed resin compound (1) at 50° C. was measured with a high shear rate viscometer (BROOKFIELD-CAP2000 H). The viscosity of the 4-armed resin compound (1) was 9.7 Pa·s at 50° C.

Synthesis Example 2

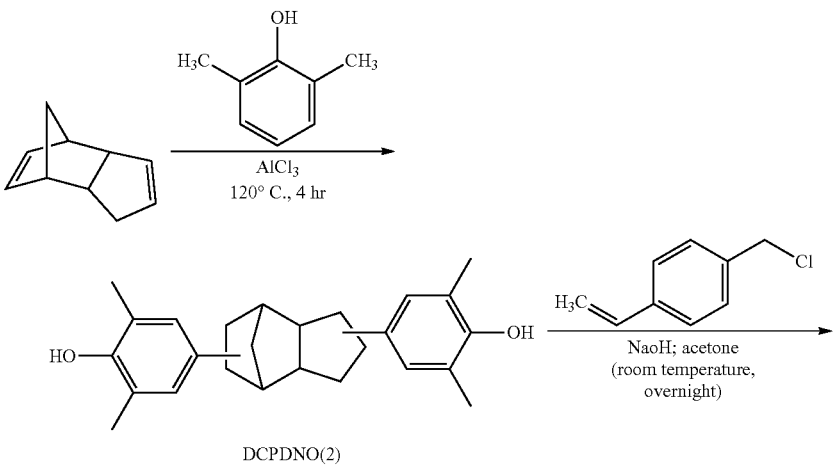

DCPDNO(2)

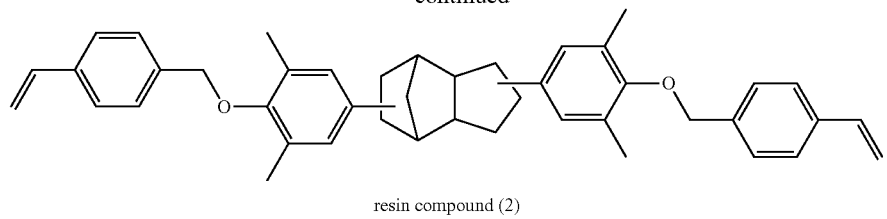

resin compound (2)

Step 1

87.3 g (0.7143 mol) of 2,6-dimethylphenol and 2 g (0.015 mol) of AlCl$_3$ were added into a 250 ml round-bottom reaction flask. The reaction flask was heated to 100° C. and the above-mentioned compounds were uniformly mixed to obtain a mixture after introducing nitrogen gas and placing a stir bar into the flask. After gradually heating the mixture to 120° C., 13.2 g (0.1 mol) of dicyclopentadiene (DCPD) was slowly added into the mixture within 2 hours, and then a reaction was conducted at 120° C. for 4 hours. After the reaction was completed, 5 mol % sodium hydroxide aqueous solution containing 2.4 g of sodium hydroxide (NaOH) was added into the mixture and the mixture was stirred for 1 hour further to obtain a reaction mixture. The resulting reaction mixture was filtered, and the filtrate was washed with water 3 times. The organic phase was distilled to remove excess 2,6-dimethylphenol, dissolved in toluene, extracted 3 times with water, and drained to obtain a dark brown solid, DCPDNO(2).

Step 2

15 g of DCPDNO(2) and 200 g of acetone were added into a 500 ml round bottom reaction flask. 1.76 g of NaOH was added and the mixture was stirred after introducing nitrogen gas and placing a stir bar into the flask. After 30 min of stirring, 13.5 g of 4-vinylbenzyl chloride was added into the flask, then a reaction was conducted at room temperature overnight. After the reaction was completed, the reaction solution was filtered to remove the solids, and the filtrate was drained to obtain a liquid product. The liquid product was analyzed by NMR, and the result shown that the liquid product was only 60% reacted.

Therefore, the obtained liquid product and 500 g of acetone were added into a 500 ml round bottom reaction flask. 1.76 g of NaOH was added and the mixture was stirred after introducing nitrogen gas and placing a stir bar into the flask. A reaction was conducted at room temperature overnight. After the reaction was completed, the reaction solution was filtered to remove the solids, and the filtrate was drained to obtain a dried crude product. The dried crude product was dissolved in dichloromethane (CH$_2$Cl$_2$), washed 3 times with water, and drained to give a dark blue-green thick liquid, a 2-arm resin compound (2).

The physical measurement of the compound 2-arm resin compound (2) is listed below: 1H NMR (500 MHz, CDCl$_3$): 1.00~2.80 (m, 26H), 4.80 (br.s, 4H), 5.31 (br.d, 2H), 5.78 (br.d, 2H), 6.45~7.15 (m, 6H), 7.48 (br.s, 8H).

The viscosity of the 2-arm resin compound (2) at 25° C. was measured with a rheometer (BROOKFIELD-87333). The viscosity of the 2-arm resin compound (2) was 147 Pa·s at 25° C. The viscosity of the 2-arm resin compound (2) at 50° C. was measured with a high shear rate viscometer (BROOKFIELD-CAP2000 H). The viscosity of the 2-arm resin compound (2) was 15 Pa·s at 50° C.

Synthesis Comparative Example 1

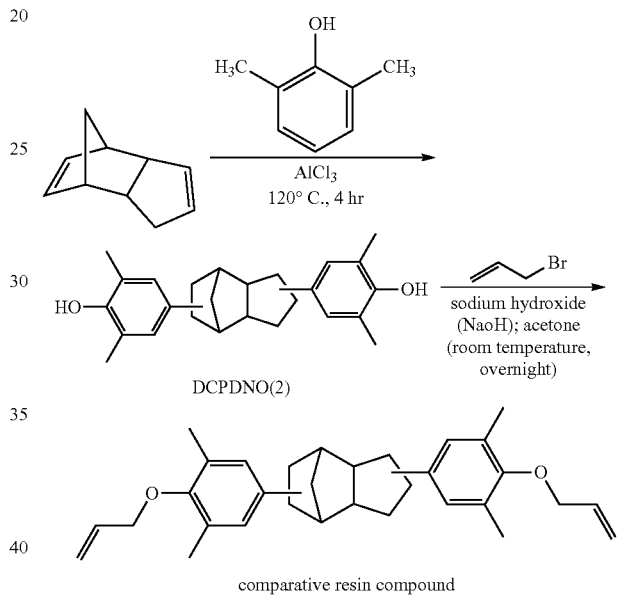

Step 1

87.3 g (0.7143 mol) of 2,6-dimethylphenol and 2 g (0.015 mol) of AlCl$_3$ were added into a 250 ml round-bottom reaction flask. The reaction flask was heated to 100° C. and the above-mentioned compounds was uniformly mixed to obtain a mixture after introducing nitrogen gas and placing a stir bar into the flask. After gradually heating the mixture to 120° C., 13.2 g (0.1 mol) of dicyclopentadiene (DCPD) was slowly added into the mixture within 2 hours, and then a reaction was conducted at 120° C. for 4 hours. After the reaction was completed, 5 mol % sodium hydroxide aqueous solution containing 2.4 g of sodium hydroxide (NaOH) was added into the mixture and the mixture was stirred for 1 hour further to obtain a reaction mixture. The resulting reaction mixture was filtered, and the filtrate was washed with water 3 times. The organic phase was distilled to remove excess 2,6-dimethylphenol, dissolved in toluene, extracted several times with water, and drained to obtain a dark brown solid, DCPDNO(2).

Step 2

35 g of DCPDNO(2) and 500 g of acetone were added into a 1000 ml round bottom reaction flask. 6.1 g of NaOH was added and the mixture was stirred after introducing nitrogen gas and placing a stir bar into the flask. After 30 min of stirring, 18.53 g(1.5N) of allyl bromide was added into the flask, then a reaction was conducted at room temperature overnight. After the reaction was completed, the reaction solution was filtered to remove the solids, and the filtrate was drained to obtain a dried crude product. The dried crude product was dissolved in dichloromethane ($CH_2Cl_2$), washed 3 times with water, and drained to give a dark brown liquid, a 2-arm comparative resin compound.

The physical measurement of the 2-arm comparative resin compound is listed below: 1H NMR (500 MHz, $CDCl_3$): 1.0~02.80 (m, 26H), 4.30 (br.s, 4H), 5.2~05.30 (m, 2H), 5.40~5.50 (m, 2H), 6.00~6.25 (m, 2H), 6.80~7.10 (m, 6H).

Preparation of Examples 1-8 and Comparative Example

The resin compound (1), the resin compound (2), the comparative resin compound, a diethylenebenzene (DVB), a 2,2-bis[3-allyl-4-(4-vinylbenzyl)phenyl]propane (AV-BPA), a toughening agent, CTBN1300*13, and a tert-butyl peroxy-3,5,5-trimethyl-hexanoate (TBPIN) were mixed in the weight ratio shown in Table 1 below to prepare compositions of Examples 1-8 and the Comparative Example. Table 1 below shows resin formulation including a combination of the resin compound and DVB or AV-BPA as a crosslinking agent, and the total weight of the combination contained in the resin formulation considered as 100 parts by weight. The amounts of the initiator (TBPIN) and the toughening agent (CTBN) were expressed in phr units, which were relative to the percentage content of the combination contained in the resin formulation. The viscosities of the compositions of Examples 1-8 and the comparative examples were measured with a rheometer (BROOKFIELD-87333) at 25° C.

AV-BPA used herein was synthesized by the following method 60 g of 85% 2,2'-diallylbisphenol A and 550 ml of acetone were added to a 1000 ml round bottom reaction flask. 15.6 g of NaOH was added and the mixture was stirred after placing a stir bar into the flask. After 30 min of stirring, 72 g of 90% 4-vinylbenzyl chloride was dropped into the flask, then a reaction was conducted at room temperature overnight. After the reaction was completed, the reaction solution was filtered to remove the solids, and the filtrate was drained to obtain a solid crystal. The resulting solid crystal were washed with methanol and dried again to give white 2,2-bis[3-allyl-4-(4-vinylbenzyl)phenyl]propane (BPA).

TABLE 1

| | Example 1 | Example 2 | Example 3 | Example 4 | Example 5 | Example 6 | Example 7 | Example 8 | Comparative Example |
|---|---|---|---|---|---|---|---|---|---|
| Resin compound (1) (wt %) | 50 | 50 | — | 70 | 40 | 25 | 10 | — | — |
| Resin compound (2) (wt %) | — | — | 50 | — | — | 25 | — | 10 | — |
| Comparative resin compound (wt %) | — | — | — | — | — | — | — | — | 50 |
| DVB (wt %) | 50 | 50 | 50 | 30 | 60 | 50 | 25 | 25 | 50 |
| AV-BPA (wt %) | — | — | — | — | — | — | 65 | 65 | — |
| TBPIN (phr) | 10 | 3 | — | 10 | 5 | 5 | 3 | 3 | 10 |
| CTBN (phr) | 5 | 5 | 3 | 5 | 5 | 5 | — | — | — |
| Viscosity (cps) | 1143 | 1235 | 1325 | 1838 | 1027 | 1316 | 2899 | 2981 | 896 |

Preparation of Cured Compositions 1-8 and Comparative Cured Composition

The compositions of Examples 1-8 and the comparative example were poured into a mold composed of two 80 mm×80 mm glass plates and a 0.5 mm thick polytetrafluoroethylene (PTFE) spacer. Those compositions were heated at 145° C. for 6 hours to obtain cured compositions 1-8 and a comparative cured composition.

Analyzing Dielectric Properties and Thermal Stability of the Cured Compositions 1-8 and the Comparative Cured Composition The dielectric constants (Dk) and dissipation factors (Df) of the cured compositions 1-8 and the comparative cured composition were measured with a vector network analyzer at 10-80 GHz. The decomposition temperatures (Td) at 5 wt % loss of the cured compositions 1-8 and the comparative cured composition were measured with a thermogravimetric analyzer (THE DSC 7 DIFFERENTIAL). The glass transfer temperatures (Tg) of the cured compositions 1-8 and the comparative cured composition were measured with a dynamic mechanical analyzer (Q800). The measured results of the formability, Td and Tg were shown in Table 2 below, where in the term of formability, O indicates the cured composition was fully cured and X indicates the cured composition was prone to brittle cracking or incomplete curing.

The dielectric constants (Dk) and dissipation factors (Df) of the cured compositions 1-8 and the comparative cured composition were measured with a vector network analyzer at 10-80 GHz, and the result was shown in Table 3 below.

TABLE 2

| | Cured composition | | | | | | | | Comparative cured composition |
|---|---|---|---|---|---|---|---|---|---|
| | 1 | 2 | 3 | 4 | 5 | 6 | 7 | 8 | |
| Formability | o | o | o | o | o | o | o | o | x |
| Td | 318° C. | 322° C. | 394° C. | 320° C. | 351° C. | 375° C. | 381° C. | 385° C. | 285° C. |
| Tg | 200° C. | 206° C. | >350° C. | — | — | — | >350° C. | >350° C. | — |

TABLE 3

| Measured frequency | | Cured composition 1 | Cured composition 2 | Cured composition 3 | Cured composition 4 | Cured composition 5 | Cured composition 6 | Cured composition 7 | Cured composition 8 |
|---|---|---|---|---|---|---|---|---|---|
| 10 GHz | Dk | 2.33 | 2.36 | 2.54 | 2.37 | 2.30 | 2.43 | 2.68 | 2.67 |
| | Df | 0.006 | 0.006 | 0.006 | 0.006 | 0.005 | 0.005 | 0.005 | 0.005 |
| 28 GHz | Dk | 2.31 | 2.32 | 2.5 | 2.36 | 2.33 | 2.45 | 2.64 | 2.65 |
| | Df | 0.005 | 0.005 | 0.006 | 0.006 | 0.005 | 0.005 | 0.006 | 0.006 |
| 38 GHz | Dk | 2.3 | 2.31 | 2.49 | 2.36 | 2.31 | 2.38 | 2.62 | 2.62 |
| | Df | 0.007 | 0.007 | 0.006 | 0.006 | 0.005 | 0.006 | 0.006 | 0.006 |
| 60 GHz | Dk | 2.3 | 2.3 | 2.48 | 2.35 | 2.3 | 2.37 | 2.59 | 2.60 |
| | Df | 0.005 | 0.006 | 0.006 | 0.006 | 0.005 | 0.006 | 0.006 | 0.006 |
| 70 GHz | Dk | 2.29 | 2.3 | 2.47 | 2.31 | 2.29 | 2.31 | 2.57 | 2.57 |
| | Df | 0.006 | 0.006 | 0.006 | 0.006 | 0.006 | 0.006 | 0.006 | 0.006 |
| 80 GHz | Dk | 2.28 | 2.29 | 2.45 | 0.3 | 2.29 | 2.32 | 2.55 | 2.53 |
| | Df | 0.006 | 0.006 | 0.006 | 0.006 | 0.006 | 0.006 | 0.006 | 0.006 |

As can be seen from Tables 1 and 2 above, the comparative cured composition formed of the resin composition comprising the comparative resin compound was prone to brittle cracking or incomplete curing. Therefore, the comparative cured composition was not suitable for application as a packaging material. In addition, according to Tables 1 and 2 above, compared to the resin composition comprising the comparative resin compound, the resin composition containing resin compound (1) and/or resin compound (1) has a higher Td. That is, compared to the resin composition comprising the comparative resin compound, the resin composition comprising the resin compound (1) and/or the resin compound (1) has better thermal stability and mechanical properties.

It can be seen from Table 3 above that the resin composition of the present disclosure has a good dielectric constant (Dk) and dissipation factor (Df) between 10-80 GHz. Accordingly, compared to the existing resin compound, the resin compound of the present disclosure can meet the requirement of low dielectric loss under high frequency due to the good dielectric properties mentioned above.

Specifically, a cured composition formed of a resin composition containing a commercially available epoxy resin HP-7200 (manufactured by Dainippon Ink and Chemicals, Inc.) having the following structure was used as Comparative Example 2. The dielectric constant (Dk) and dissipation factor (Df) of the cured composition of Comparative Example 2 at 1 GHz were measured according to the same method as shown above, and the dielectric constant (Dk) of Comparative Example 2 at 1 GHz was 3.24 and the dissipation factor (Df) was 0.02. It is clear that, according to Table 3 above, the dielectric constant (Dk) of the resin compositions of the present disclosure at 10-80 GHz are lower than the dielectric constant (Dk) of Comparative Example 2 at 1 GHz. The dissipation factor (Df) of the resin compositions of the present disclosure at 10-80 GHz are lower than the dissipation factor (Df) of Comparative Example 2 at 1 GHz. Accordingly, compared to the existing resin compounds, the resin compound of the present disclosure may reduce the dielectric loss in high-frequency applications, thereby improving the signal emission and reception quality.

HP-7200

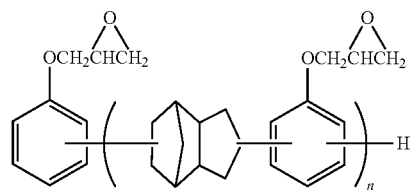

While the disclosed embodiments has been described by way of example and in terms of the preferred embodiments, it should be understood that the disclosed embodiments is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A resin compound having a structure represented by chemical formula (II):

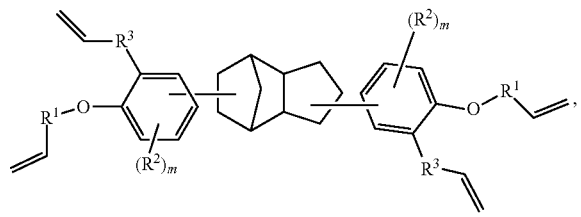

(II)

wherein each $R^1$ independently represents a $C_1$-$C_{20}$ alkylene group or a $C_7$-$C_{40}$ alkylarylene group;
each $R^2$ independently represents a $C_1$-$C_{20}$ alkyl group or a $C_2$-$C_{20}$ terminal alkenyl group, and
each $R^3$ independently represents a single bond or a $C_1$-$C_{18}$ alkylene group;
m independently represents an integer of 0-3, and
each $R^1$, $R^2$, and $R^3$ are the same or different from each other.

2. The resin compound as claimed in claim 1, wherein each $R^1$ independently represents a $C_1$-$C_6$ alkylene group or a $C_7$-$C_{10}$ alkylarylene group, and each $R^2$ independently represents a $C_1$-$C_6$ alkyl group or a $C_2$-$C_6$ terminal alkenyl group.

3. The resin compound as claimed in claim 1, wherein each $R^2$ independently represents a methyl group, an ethyl group, a propyl group, an iso-butyl group, a sec-butyl group, a tert-butyl group, a pentyl group, an iso-amyl group, a hexyl group, an ethenyl group, a 2-propenyl group, or a 1-butenyl group.

4. The resin compound as claimed in claim 1, wherein the resin compound has a structure represented by chemical formula (II-1):

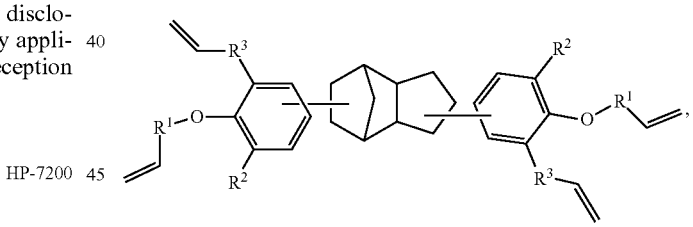

(II-1)

wherein each $R^1$ independently represents a $C_1$-$C_{20}$ alkylene group or a $C_7$-$C_{40}$ alkylarylene group;
each $R^2$ independently represents a $C_1$-$C_{20}$ alkyl group;
each $R^3$ independently represents a $C_1$-$C_{18}$ alkylene group, and
each $R^1$, $R^2$, and $R^3$ are the same or different from each other.

5. A resin composition, comprising the resin compound as claimed in claim 1 and a crosslinking agent.

6. The resin composition as claimed in claim 5, wherein the crosslinking agent is selected from a group consisting of a divinylbenzene (DVB), a 4-tert-butoxystyrene (tBOS), a triallyl isocyanurate (TAIC), a triallyl cyanurate (TAC), and a 2,2-bis [3-allyl-4-(4-vinylbenzyl)phenyl]propane (AV-BPA).

7. A resin composition, comprising the resin compound as claimed in claim 2 and a crosslinking agent.

8. A resin composition, comprising the resin compound as claimed in claim 3 and a crosslinking agent.

9. A resin composition, comprising the resin compound as claimed in claim 4 and a crosslinking agent.

\* \* \* \* \*